United States Patent [19]

Khachatourians

[11] 4,311,797

[45] Jan. 19, 1982

[54] ANUCLEATED LIVE E. COLI VACCINE

[75] Inventor: George G. Khachatourians, Saskatoon, Canada

[73] Assignee: University of Saskatchewan, Saskatoon, Canada

[21] Appl. No.: 76,610

[22] Filed: Sep. 18, 1979

[51] Int. Cl.$^3$ .............................................. C12N 15/00
[52] U.S. Cl. .................................. 435/172; 435/253; 435/820; 424/92
[58] Field of Search .............................. 435/172, 253

[56] References Cited

U.S. PATENT DOCUMENTS 3,839,556 10/1974 Mebus et al. ........................... 424/89
3,907,987 9/1975 Wilson .................................... 424/92

OTHER PUBLICATIONS

Veterinary Medicine/Small Animal Clinician, Mar. 1978, p. 371.
Cohen et al, Proc. Nat. Acad. Sci., vol. 61, pp. 61–68, (1968).
Veterinary Infectious Disease Organization, Viewing VIDO, No. 8 (Saskatoon, Saskatchewan, Canada, Mar. 1978).
Bonner et al, Clinical Research, vol. 24:1, p. 24A, (Jan. 1976).
Coyne et al, Infection and Immunity, vol. 12, No. 5, pp. 1189–1194, (Nov. 1975).
Acres, Veterinary Infectious Disease Organization Annual Report, Apr. 1–1977 to Mar. 31, 1978, (pp. 10–12).
Chakrabarty, Genetic Engineering, CRC Press, p. 13, (1978).
Tankersley et al, Proc. Soc. for Exptl. Biology and Medicine, 145, pp. 802–805, (1974).
Lewin, Gene Expression, John Wiley & Sons, vol. 3, pp. 140–142, (1977).
Beale et al, Extranuclear Genetics, University Park Press, pp. 71 and 72 (1978).

*Primary Examiner*—Alvin E. Tanenholtz
*Attorney, Agent, or Firm*—Depaoli & O'Brien

[57] ABSTRACT

An *E. coli* strain producing metabolically active but non-reproductive, anucleated live cells, which contain the K99 surface antigen, is obtained by transferring the K99 plasmid from a K99+ entero pathogenic *E. coli* strain into an *E. coli* strain which generates progeny of cells that lack the ability to multiply. From the resulting *E. coli* strain a "live" vaccine is prepared. Separation and purification of the anucleated live cells from growing cells is the basis for the "live" and chemically and/or physically unmodified vaccine. The vaccine induces the production of antibodies against growing and infective enteropathogenic K99+ *E. coli* in cattle and is, thus effective against coliform enteritis.

23 Claims, No Drawings

ANUCLEATED LIVE E. COLI VACCINE

This invention relates to the production of an *Escherichia coli* (*E. coli*) strain which produces metabolically active, non-reproductive anucleated live K99+ *E. coli* cells.

This invention further relates to a vaccine which contains anucleated live K99+ *E. coli* cells and is effective against enteropathogenic colibacillosis. Inability of these anucleated live K99+ *E. coli* cells to multiply in vitro and to infect animals is shown.

This invention further relates to the technique of preparing high yields of anucleated live K99+ *E. coli* cells, their purification and concentration.

This invention further relates to the method of using anucleated live K99+ *E. coli* cells to induce the production of antibodies against enteropathogenic *E. coli*, thereby immunizing cattle against enteropathogenic colibacillosis.

Enteric colibacillosis vaccines against *E. coli* have been prepared in the past by growing of the pathogenic bacteria and weakening or killing them with chemical or physical agents. Such bacteria become devoid of infective qualities or have smaller probability of causing an infection.

Among references of interest are the following: U.S. Pat. No. 3,907,987 issued Sept. 23, 1975; L. L. Myers, Am. J. Vet. Res. (1976) 37: 831–834.

It is common knowledge that chemical treatment of bacteria will drastically affect those cell surface constituents that are essential in the immune response created in vaccinated animals. Therefore vaccines containing inactivated bacteria have lesser potential in eliciting lasting immunity to the disease than a vaccine containing anucleated live *E. coli* cells. It is desirous to obtain by genetic means an *E. coli* strain which produces metabolically active, anucleated live cells which contain surface antigenic complements, but which are unable to propagate themselves and infect animals being vaccinated. Such cells, by definition, will not need killing or inactivation by physical and/or chemical agents and can be used as "live" vaccines. These "live" vaccines can induce an immune response to the specific surface antigen which is carried by the minicells without infecting the animal. "Live" vaccines may, therefore, become widely applicable in animal as well as human disease prophylaxis.

To produce a "live" vaccine against enteropathogenic *E. coli* it is, therefore, necessary to obtain metabolically active but non-reproductive, anucleated live *E. coli* cells which contain the surface antigen $K_{99}$ common to *E. coli* strains which cause neonatal diarrhea in calves.

Strains of microorganisms such as *E. coli*, which produce metabolically active but non-reproductive, anucleated live cells (minicells) are known in the art (see W. G. Tankersley et al., Proc. Soc. Exp. Biol. Med. (1974) 145:802–805). During the reproduction of such an *E. coli* strain the parental cells will generate two different sets of offspring. Instead of dividing in the middle of the cell to form equally-sized daughter cells which grow to form full-size *E. coli*, this mutant of *E. coli* divides very close to the pole of the cell, thereby giving one very small cell, called a minicell, and one very large cell. The minicells are live and metabolically active yet are unable to reproduce, because they do not have a nucleus. The large cells, on the other hand, contain a nucleus and are reproductive. A strain of *E. coli* which reproduces by dividing into a minicell and a regular cell will be called "minicell-producing *E. coli*". For every $10^9$ viable cells in a culture, at least $10^9$ anucleated cells (minicells) are produced. These live anucleated and non-reproductive cells accumulate in the culture.

Minicell producing *E. coli* strains which contain the surface antigen K99, common to the strains of *E. coli* which are the causative bacteria of neonatal diarrhea in calves (enteropathogenic *E. coli*) have not been found in nature but have been constructed according to the present invention. Viable cells as well as minicells from these *E. coli* strains have K99 pili on their surface. To obtain an *E. coli* strain which produces anucleated live K99+ *E. coli* cells, the K99 plasmid from a strain of enteropathogenic *E. coli* was transferred into a minicell-producing *E. coli* parent strain whereby specific mating conditions and selection scheme allow for the formation of minicell-producing K99+—containing *E. coli* cells. The resulting minicell-producing K99+ *E. coli* strain (internal identification number GK500) and derivatives thereof are being maintained at the University of Saskatchewan, College of Medicine, Department of Microbiology, Saskatoon, Saskatchewan, S7N 0W0, Canada. It contains a serotype of K99+:K12+:0101: H and two unique features. The sample of this strain has been deposited with the American Type Culture Collection, Rockville, Maryland. Received there September 10, 1979 and recorded under American Type Culture Collection No. 31563.

Antiserum prepared against this minicell-producing K99+ *E. coli* strain reacts against other related *E. coli* strains associated with neonatal diarrhea in calves.

It is an object of the invention to provide a method of making an *Escherichia coil* (*E. coli*) strain, preferably *E. coli* GK 500, which produces metabolically active, non-reproductive, anucleated live K99+ *E. coli* cells comprising the steps of:

(a) mixing an *E. coli* strain which produces metabolically active, non-reproductive, anucleated live cells (minicells) with a K99+ enteropathogenic *E. coli* strain;

(b) incubating the mixed cells in a culture medium, preferably at a cell density of approximately $2-3 \times 10^8$ cells/ml culture medium and preferably at 37° for about 18h;

(c) separating minicell-producing *E. coli* cells which contain the K99 plasmid from other cells in the culture medium;

(d) growing the separated minicell-producing K99+ *E. coli* in a second culture medium, preferably on agar plates containing streptomycin and more preferably on agar plates containing 200 µg/ml streptomycin.

It is a further object of the invention to provide a method of making a vaccine which contains metabolically active, non-reproductive anucleated live K99+*E. coli* cells and which is useful for preventing neonatal diarrhea in cattle comprising the steps of:

(a) transferring the K99 plasmid from an enteropathogenic *E. coli* strain into a minicell-producing *E. coli* strain;

(b) growing the resulting minicell-producing K99+ *E. coli* strain in broth culture medium under aerobic conditions with agitation, whereby it is preferred to select colonies of minicell-producing K99+ *E. coli* GK 500 and to grow them in a minimal salts based synthetic medium for 15 to 18 hours at 36° to 37.5° C., most preferably at 37° C.;

(c) separating the bacterial cells from the broth culture medium by centrifugation and suspending them, preferably in a buffered salt solution;

(d) separating minicells from complete reproductive cells by sucrose gradient centrifugation, whereby the preferred method is the following:

layering the suspension containing the bacterial cells on a first sucrose gradient, which preferably comprises a 5% sucrose solution layered over a 20% sucrose solution, and centrifuging;

collecting and concentrating the top fractions of the first sucrose gradient;

layering the concentrated fractions on a second sucrose gradient, which preferably comprises a linear sucrose gradient of 10-5% layered over a 10% sucrose solution, and centrifuging; and collecting, combining and concentrating the top fractions of the second sucrose gradient.

The combined concentrated top fractions of the second sucrose gradient may be further purified by freezing said concentrated fractions at $-20°$ C., preferably for at least 2 to 3 days, more preferably for 9 to 10 days, followed by thawing slowly at $20°$-$22°$ C. and by centrifuging the thawed suspension and resuspending the pellet, preferably in a buffered salt solution.

Alternatively the combined concentrated top fractions of the second sucrose gradient may be further purified by incubating said concentrated fractions in brain heart infusion broth, preferably at $36°$ to $38°$ C. for 1 hour, followed by the addition of penicillin G, preferably to the concentration of 0.5-1.0 mg/ml, further incubation, preferably at $36°$ to $38°$ C. for at least 1.5 hours, more preferably for 2 hours, and centrifugation of the incubated suspension and resuspension of the pellet, preferably in a buffered salt solution.

It is a further object of the invention to provide a bacterial vaccine for inducing immunity by promoting the formation of antibodies against enteropathogenic K99+ $E.$ $coli$ in cattle comprising an aqueous suspension containing metabolically active but non-reproductive anucleated live cells (minicells) of a K99+ $E.$ $coli$ strain preferably of $E.$ $coli$ of serotype K99+:K12+: 0 101:H, and most preferably of $E.$ $coli$ GK500.

In a preferred embodiment said vaccine comprises an aqueous suspension which is stable for at least 3 months and which contains between $10^{12}$ and $10^{13}$ minicells/ml and less than one reproductive cell per $10^6$ anucleated cells. Preferably the antigenicity of the vaccine is dependent on the presence of K99 antigen on the surface of the minicells.

It is a further object of the invention to provide a method of preventing neonatal diarrhea in calves comprising the step of administering to the pregnant cow prior to parturition, preferably at least one week prior to parturition and more preferably about 6 weeks and again about 3 weeks prior to parturition, a vaccine which contains metabolically active, non-reproductive, anucleated live cells (minicells) of a K99+ $E.$ $coli$ strain, preferably of $E.$ $coli$ of serotype K99+:K12+:0 101:H, and more preferably of $E.$ $coli$ GK500, whereby to induce in the cow effective blood and colostral levels of antibodies against enteropathogenic $E.$ $coli$.

In a preferred method the vaccine administered to the pregnant cow contains between $10^{12}$ and $10^{13}$ minicells/dose and more preferable $9 \times 10^{12}$ minicells/dose.

The minicell-producing K99+ $E.$ $coli$ strains such as $E.$ $coli$ GK500 according to the invention are obtained by co-cultivation of a minicell-producing $E.$ $coli$ parent strain and a K99+ enteropathogenic $E.$ $coli$ strain. The mating process is started by mixing the two $E.$ $coli$ strains at a cell density of approximately $2$-$3 \times 10^8$ cells/ml nutrient broth medium at $37°$ C. in a large, flat bottomed flask. After about 18 hours of co-incubation the K99 plasmid can be found to be transferred to the minicell-producing bacteria at a frequency of approximately one in every 3000. These minicell-producing K99 containing cells are plated on Penassay Agar (trademark) plates containing 200 µg/ml streptomycin. Thousands of colonies are selected and each colony is replated and tested for the K99 surface antigen.

The vaccine according to the invention is prepared by growing $E.$ $coli$ strains which produce good yields of anucleated live K99+ $E.$ $coli$ cells (ALEC). Stock cultures of these strains are maintained on Penassay Agar slants and checked periodically for genetic stability by streaking on MacConkey Agar (trademark) plates containing streptomycin. These strains are lactose non-fermenting types and grow in the presence of streptomycin. Cultures must show K99 positive agglutinations in slide agglutination tests. The strains can be started in brain heart infusion broth. Following incubation, a loopful of culture from the brain heart infusion broth is streaked onto Penassay Agar plates and incubated. Several colonies showing a "zig-zag" surface colonial morphology are mixed with a drop of known K99 standard antiserum. This is to ensure the stability of the K99+ character of the strains in use. Every one of the colonies tested must show strong agglutination with this antiserum before it is to be used for preparation of ALEC vaccine.

Standard rabbit serum containing anti-K99 antibodies is obtained by repeated injection of K99+ WHO standard $E.$ $coli$ K99+ strain B41 into adult female rabbits and bleeding subsequent to the last injection.

A medium which may be used for the growth of $E.$ $coli$ strains is a minimal salts based synthetic medium containing $NH_4Cl$, $NH_4NO_3$, $Na_2SO_4$, $K_2HPO_4$, $KH_2PO_4$, $MgSO_4 \cdot 7H_2O$, casamino acids, glycerol and vitamin $B_1$ in aqueous solution. This growth medium is distributed in flasks such that the ratio of flask volume (FV) to liquid volume (LV) is 10:2 or less. A FV:LV ratio other than this will reduce the aeration rate and, consequently, the yield of ALEC. The growth flasks containing said growth media are seeded with approximately 0.5% (v/v) of starter brain heart infusion broth culture and incubated for 15-18 hours at $36°$-$37.5°$ C. in a water bath under shaking. At the end of the period a culture density of 1.3 to 1.5 O D units (600 nm) of cells, as measured spectrophotometrically (Spectronic 20, trademark), is obtained. The number of viable cells is about $0.8$-$1 \times 10^9$ bacteria/ml. The cell cultures are centrifuged in conventional centrifuges. Clear supernatants are discarded and the pellets are suspended in a small amount of a Buffered Salts solution. Said Buffered Salts solution is comprised of: $NaCl_2$, $KH_2PO_4$ anhydrous, $Na_2HPO_4$ anhydrous, gelatin and distilled water.

To separate ALEC cells from the whole cells about 2 to 2.5 ml of concentrate may be placed on top of a shelf gradient containing a combination of about 5 ml solution of 5% (w/v) sucrose layered over approximately 20 ml of 20% (w/v) sucrose. Sucrose solutions are made in the Buffered Salts solution, sterilized and kept at $4°$ C. Shelf sucrose gradient tubes containing the concentrations are placed in an IEC (trademark) swinging bucket centrifuge and spun at 2700 rpm for 16 minutes at room temperature. The same operation can be run in a Sorval SS-3 (trademark) centrifuge at 3,000 rpm for 8 minutes, using an HB-4 (trademark) head.

The top 3 fractions (fractions A, B and C) having densities of between 0.3 and 0.5 O D units, preferably of between 0.4 and 0.5 O D units (600 nm), and viable cell counts of between $3 \times 10^6$ and $6 \times 10^6$ per ml are gently collected from the top of the gradient using a pasteur pipette or a syringe with a 18 gauge needle, bent at right angle near the tip. The combined fractions are delivered into a plastic centrifuge tube. This material is pelleted in a conventional centrifuge and resuspended in 1 to 2 ml of Buffered Salts solution. Combination sucrose gradients are made for the final preparation and purification of ALEC. The gradients may be prepared by placing about 10 ml of 10% (w/v) sucrose in culture tubes. On top of this, approximately 20 ml of linear sucrose gradient of 10–5% is delivered using a double chamber gradient maker device and a Technicon (trademark) proportioning pump. Gradients are produced and stored at 4° C. until use and can be kept for no longer than 2 hours. Two to 3 ml of combined concentrated fraction A, B and C are placed on the gradient and tubes are spun for 16 minutes at 2,700 rpm in an IEC swinging bucket head. The top 2 fractions (I and II) are collected, centrifuged and the pellets resuspended in Buffered Salts solution. An actual count of viable material in bands I and II shows about $10^8-10^9$ ALEC to $7-10 \times 10^2$ whole cells per ml, i.e. less than 1 whole cell per $10^6$ ALEC cells. The number of whole bacterial cells is directly related to the amounts of band C material removed when preparing the concentrate to be used for the second sucrose gradient. It is desirable to remove only bands A and B although this will reduce the yields. The amount of contaminating whole bacteria can be further reduced in one of two ways: either by freezing the final ALEC preparation at $-20°$ C. and thawing slowly; or by incubation of said purified preparation in brain heart infusion broth at 36°–38° C. followed by the addition of penicillin G and further incubation. This is followed by centrifugation and resuspension of ALEC pellets in Buffered Salts solution. ALEC vaccine preparations are stored at $-20°$ C.

The vaccine according to the invention is normally administered or injected parenterally (subcutaneously, intramuscularly or intramammary). It is normally administered to the pregnant cow at least one week prior to parturition, and preferably in a series of 2 doses about 3 and 6 weeks before calving.

Dosage will vary from about 2 to 10 ml depending on the concentration of ALEC cells in the suspension. The vaccine will usually have an optical density of about 1.0 at 600 nm. Each dose contains between $10^{12}$ and $10^{13}$ ALEC cells.

Prior to the vaccination the suspension of ALEC cells in Buffered Salts solution may be combined with an adjuvant such as Freund's Complete Adjuvant, aluminium potassium sulfate or other suitable adjuvants known in the art.

The vaccine according to the invention is evaluated by vaccinating cows and rabbits and studying the serologic response. Whereby the results obtained from rabbits are valid for cows.

Female rabbits are immunized with a series of 3–5 subcutaneous injections of ALEC mixed v/v with Freund's Complete Adjuvant (obtained from Difco). At weekly intervals blood is removed from the marginal ear vein, and the serum separated. Titers are determined by the standard agglutinations method of Edwards and Ewing (Burgess Publishing Co., Minneapolis, 1972). The bacterial suspension used in agglutination tests is 0.75 OD units. This standard is kept throughout. The immunogenicity of the ALEC cell preparation in rabbits is determined. Control tests consist of serum taken from rabbits before the immunization schedule.

Cows are injected with ALEC cells. About twenty-one days later their blood is collected and the serum obtained. Bacterial agglutination tests are run using sera against *E. coli* strains from cows and rabbits.

The amount of vaccine according to the invention which is necessary for the production of an immune response is measured in rabbits. Various dilutions of the ALEC preparation with Buffered Salts solution are prepared before mixing with Freund's Complete Adjuvant. Rabbits are immunized subcutaneously. Animals are bled two weeks after the last injection and the antibody titers are determined.

The vaccine according to the invention is further evalutated by feeding colostrum from vaccinated cows to calves which have been exposed to infection under controlled conditions. Preferably, newborn calves are challenged orally with viable cells of enteropathogenic *E. coli* strains. When these calves receive colostrum containing effective levels of antibodies against enteropathogenic *E. coli*, they develop a high extent of immunity to neonatal diarrhea.

The stability of the vaccine on storage is determined by injecting rabbits with ALEC preparations which have been stored for up to 3 months. When the resulting antibody titres are compared with antibody titres induced by vaccination with fresh ALEC preparations, the values are practically identical. This result shows that ALEC vaccine is stable for a period of at least 6 weeks when stored at 4° C. and for a period of at least 3 months when stored at $-20°$ C. Furthermore ALEC preparations do not regenerate any viable colony forming cells while stored in said manner.

Theimmunogenicity against K99 antigen of the vaccine according to the invention was evaluated by subjecting the ALEC preparation to mechanical shearing by sonication. As K99 is located on the surface of ALEC cells in the form of long fimbriae type structures, sonication removes most of the K99 antigen from the ALEC cells. The sonicated sample is centrifuged and the resuspended pellet is injected into rabbits. Comparison of agglutination tests, performed with sera from animals injected with sonicated and unsonicated ALEC vaccine, respectively, show that mechanical shearing reduced the immunogenicity of the ALEC vaccine considerably.

The following examples are given in illustration of, but not in limitation of the present invention.

EXAMPLE 1

Three strains identified as *E. coli* strains were tested and produced good yields of ALEC. Stock cultures of these strains were maintained on Penassay Agar slants at 4° C. and checked periodically for genetic stability by streaking on MacConkey Agar plates containing 50 μg/ml streptomycin. Cultures must show K99 positive agglutination in slide agglutination tests. The strains are started in brain heart infusion broth. Following incubation for 15 hours, a loopful of culture from brain heart infusion broth is streaked onto Penassay Agar plates and these are incubated at 37° C. for 24 hours. Several (10–20) colonies showing a "zig-zag" surface colonial morphology were picked off with a sterile toothpick and mixed with a drop of known K99 standard antisera. This is to ensure the stability of the K99+ character of the strains in use. Every one of 10-20 colonies tested showed strong agglutination with this antiserum before it was used for preparation of ALEC vaccine. Standard rabbit serum containing antibodies was obtained by repeated injection of K99+ WHO standard *E. coli* K99+ strain B41 into adult female rabbits and bleeding subsequent to the last injection and separation of serum from blood clots.

EXAMPLE 2

The medium used for the growth of *E. coli* strains is a minimal salts based synthetic medium. It contains: $NH_4Cl$ (10 g), $NH_4NO_3$ (2 g), $Na_2SO_4$ (4 g), $K_2HPO_4$ (18 g), $KH_2PO_4$ (6 g), $MgSO_4 \cdot 7H_2O$ (0.2 g), 1000 ml distilled $H_2O$. This medium is mixed volume per volume (v/v) with sterile $H_2O$ containing 20% (weight-/volume) casamino acids, 2.0% glycerol (w/v) and vitamin $B_1$ (5 µg/ml). This growth medium is distributed in flasks such that the ratio of flask volume (FV) to liquid volume (LV) is 10:2 or less, i.e. 5 or 10. A FV:LV ratio other than these will reduce the aeration rate and consequently, the yields of ALEC. The growth flasks containing said growth media are seeded with 0.5% (v/v) of starter brain heart infusion broth culture and incubated for 15-18 hours at 37° C. in a water bath shaking at 180-220 rpm. At the end of the period a culture density of 1.3 to 1.5 OD units (600 nm) of cells, as measured spectrophotometrically (Spectronic 20) is obtained. The number of viable cells is about $0.8-1 \times 10^9$ bacteria/ml. The cell cultures are centrifuged in conventional centrifuges at $10,000 \times g$ for 15 minutes. Clear supernatants are discarded and the pellets are suspended in Buffered Salts solution at 1/20 of the original volume. The Buffered Salts solution is comprised of: $NaCl_2$ (17 g), $KH_2PO_4$ anhydrous (0.6 g), $Na_2HPO_4$ anhydrous (1.2 g), gelatin (1% stock solution; 20 ml) and distilled water, 2000 ml.

EXAMPLE 3

To purify ALEC from the whole culture, 2 to 2.5 ml of concentrate is placed on top of a shelf gradient in pyrex culture tubes which contain a combination of 5 ml solution of 5% (w/v) sucrose layered over 20 ml of 20% (w/v) sucrose. Sucrose solutions are made in the Buffered Salts solution, sterilized and kept at 4° C. Shelf sucrose gradient tubes containing the concentrates are placed in an IEC swinging bucket centrifuge and spun at 2700 rpm for 16 minutes at room temperature. Table 1 shows the results of one of these runs in an IEC centrifuge.

TABLE 1

| Fraction Number | Volume* | Location** | OD*** | Viable Cell Count per ml |
|---|---|---|---|---|
| A (top) | 0.9 | 7.4 | 0.480 | $5.2 \times 10^6$ |
| B | 3.2 | 6.9 | 0.435 | $3.2 \times 10^6$ |
| C | 2.6 | 6.1 | 0.355 | $4.8 \times 10^6$ |
| D | 13.9 | 5.3 | 1.170 | $2.3 \times 10^{10}$ |
| E (bottom) | 4.8 | 1.7 | 1.780 | $3.9 \times 10^{10}$ |

*in ml
**cm from the bottom of centrifuge tube
***OD at 600 nm using Spectronic 20

Fractions A, B, and C are gently collected from the top of the gradient using a pasteur pipette or a syringe with a 18 gauge needle, bent at right angle near the tip. The combined fractions are gently delivered into a plastic centrifuge tube. This material is pelleted at $10,000 \times g$ in a conventional centrifuge for 10 minutes and resuspended in 1.5 ml of Buffered Salts solution.

EXAMPLE 4

Combination sucrose gradients are made for the final preparation and purification of ALEC. The gradients are prepared by placing 10 ml of 10% (w/v) sucrose in pyrex culture tubes. On top of this, 20 ml of linear sucrose gradient of 10-5% mixture is delivered using a double chamber gradient maker device and a Technicon proportioning pump. Gradients are produced and stored at 4° C. until use and can be kept for no longer than 2 hours. 2.5 ml of concentrated fraction A, B, and C are placed on each gradient and tubes are spun for 16 minutes at 2,700 rpm in an IEC swinging bucket head. Table 2 shows the results of one such preparation.

TABLE 2

| Fraction Number | Volume of Fraction (ml) | Location (cm) | OD (600 nm) |
|---|---|---|---|
| I | 1.5 | 8.6 | 0.34 |
| II | 5.2 | 8.0 | 0.59 |
| III | 4.0 | 7.0 | 0.27 |
| IV & V | 20.0 | 5.8 | 0.005 |

Material from fractions I and II is centrifuged and resuspended in Buffered Salts solution and kept at 0° to −20° C. An actual count of viable material in bands I and II shows about $10^8-10^9$ ALEC to $7-10 \times 10^2$ whole cells per ml. i.e. less than 1 whole cell per $10^6$ ALEC cells. The number of whole bacterial cells is directly related to the amounts of band C material (in Example 3) removed when preparing the concentrate to be used for the second sucrose gradient. It is desirable to remove only bands A and B although this will reduce the yields. The amount of contaminating whole bacteria can be further reduced in one of two ways: by freezing the final ALEC preparation at −20° C. in a freezer preferably for 2-3 days and most preferably for 9-10 days and thawing slowly at room temperature of 20°-22° C.; or by incubation of said purified preparation in brain heart infusion broth at 36°-38° C. for 1 hour followed by the addition of 0.5-1.0 mg/ml of penicillin G and further incubation for at least 90 minutes and preferably for 120 minutes at 36°-38° C. This is followed by centrifugation and resuspension of the ALEC pellets collected from such centrifugation procedures in Buffered Salts solution. ALEC vaccine preparations are then stored at −20° C. until such time as needed.

EXAMPLE 5

Adult female rabbits weighing between 2-3 kg were obtained from the University Animal Resources Centre. They were fed ad libitum. Rabbits were immunized with a series of 3-5 subcutaneous injections containing sequentially 0.4, 0.4 and 0.8 and 1.6 ml of ALEC mixed v/v with Freund's Complete Adjuvant (Difco). Injections were made in the nuchal region. The amount of ALEC used in this mixture was 1.0 OD units at 600 nm. At weekly intervals blood was removed from the marginal ear vein, allowed to clot at 37° C. and placed in the refrigerator for 12-16 hours. Serum was then separated from the clot. Titers were determined by the standard agglutination method of Edwards and Ewing. The bacterial suspension used in agglutination tests was 0.75 OD units. This standard is kept throughout. Control tests consisted of serum taken from rabbits before the immunization schedule. Immunogenicity of ALEC in rabbits is shown in Table 3. Results reported in this example confirm that rabbits injected with ALEC can produce antibodies against whole cells of E. coli K99+:K12+ serotypes. None of the injected rabbits have developed an E. coli infection in situ.

TABLE 3

| Sera Collection Day | Reciprocal of agglutination titres | |
| --- | --- | --- |
| | GK 500 | GK 542 (B 41) |
| 0 | 0 | 0 |
| 7 | 8 | 16 |
| 15 | 128 | 128 |
| 24 | 512 | 512 |
| 32 | 1024 | 1024 |
| 35 | 2048 | 2048 |
| 40 | 2048 | 2048 |

EXAMPLE 6

Cows were injected with ALEC. Twenty-one days later their blood was collected and the serum was obtained. Bacterial agglutination tests were run using sera against E. coli strains from cows and rabbits. Results are shown in Table 4 indicating that immune sera from ALEC injected animals contain positive agglutination material.

TABLE 4

| E. coli Strain | K99 + K12 Serotype | Agglutination of cells with ALEC antiserum | |
| --- | --- | --- | --- |
| | | cow antiserum | rabbit antiserum |
| GK 294 | + | + | + |
| GK 465 | + | + | + |
| GK 500 | + | + | + |
| GK 502 | + | + | + |
| GK 542 (B41) | + | + | + |
| GK 100 | − | − | − |
| GK 19 | − | − | − |

EXAMPLE 7

ALEC dosage necessary for the production of an immune response in rabbits was measured. ALEC preparation at OD of 1.2 (600 nm) was diluted 1:100 and 1:10,000 with Buffered Salts solution before mixing with Freund's Complete Adjuvant. Rabbits were immunized subcutaneously as before with 0.2, 0.4, and 0.8 ml of the vaccine preparation. Animals were bled two weeks after the last injection. Table 5 shows the results of these tests indicating 8–10-fold reduction in the antibacterial immune serum titres for every 100-fold dilution of ALEC.

TABLE 5

| ALEC Vaccine Preparation | Final Antibody Titre |
| --- | --- |
| Undiluted | 2560 |
| Diluted: | |
| 1:100 | 320 |
| 1:10,000 | 40 |

EXAMPLE 8

Nine cows were given subcutaneously 5 ml ALEC cell vaccine containing $9 \times 10^{12}$ minicells in aluminum potassium sulfate adjuvant. Each cow was inoculated twice, approximately three and six weeks before parturition. Ten other cows were left as unvaccinated controls. Following parturition, calves were allowed to nurse their dams and when 12–14 hours old were challenged orally with $10^{11}$ cells of enteropathogenic E. coli strain B44. The results are shown in Table 6.

TABLE 6

OCCURENCE OF SCOURS AND DEATH IN CALVES WHOSE DAMS WERE VACCINATED WITH ALEC CELL VACCINE

| VACCINE GIVEN TO COWS | NUMBER OF CALVES | |
| --- | --- | --- |
| | Diarrheic | Died |
| None | 10/10 | 9/10 |
| ALEC | 3/9 | 1/9 |

EXAMPLE 9

Three 5 ml ALEC samples, prepared as in Example 2, were stored at 4° C. for 6 weeks and at −20° C. for 6 weeks and 3 months respectively. Samples were thawed, mixed with equal volumes of Freund's Complete Adjuvant and injected into rabbits as in Example 5. Serum antibody titers to whole bacterial cells were determined by standard agglutination tests.

Immune sera from cold stored ALEC preparations contained the same antibody titres of 1:2560 as those from fresh preparations. This result shows that the ALEC vaccine is stable when stored at 4° C. for at least 6 weeks and at least 3 months when stored at −20° C. Stored ALEC cells were streaked onto Penassay Agar plates and incubated. No colony-forming cell types were detected, i.e. ALEC preparations did not regenerate any viable (colony-forming) cell types on storage.

EXAMPLE 10

The K99 antigen on the surface of ALEC is in the form of long fimbriae type structures. The sensitivity of the K99 antigen of ALEC vaccine to extreme conditions of mechanical shear was tested. A 5 ml sample of K99 ALEC prepared as directed in Example 2 was subjected to 2 minutes (in 4 times 30 second pulses) of ultrasound treatment at 4° C. using a Braunsonic (trademark) 1510 sonicator, as a setting of 100 watts, using a medium size sonicator tip. At the end of the treatment, the sonicated ALEC sample was spun down at 7,000 rpm for 10 minutes in a Sorval centrifuge. The pelleted ALEC was resuspended in 30 ml of Buffered Salts solution and centrifuged a second time. Rabbits were injected with 4 doses of 0.4, 0.4, 0.8, and 1.6 ml of ALEC vaccine preparation as in Example 5. The results of immunization are tabulated below in Table 7.

TABLE 7

| Treatment | Agglutination Titre |
| --- | --- |
| Unsonicated | 1:2048–1:4056 |
| Sonicated | 1:256–1:512 |

This result shows susceptibility of the K99 antigen of AIEC to extremes of physical shearing and that under such treatments its immunogenicity is reduced.

I claim:

1. A method of making an *Escherichia coli* (*E. coli*) strain which produces metabolically active, non-reproductive, anucleated live K99+*E. coli* cells comprising the steps of:

mixing an *E. coli* strain which produces, metabolically active, non-reproductive, anucleated live cells (minicells) with a K99+ enteropathogenic *E. coli* strain;

incubating the mixed cells in a culture medium;

separating minicell-producing *E. coli* cells which contain the K99 plasmid from other cells in the culture medium; and growing the separated minicell-producing K99+*E. coli* in a second culture medium.

2. A method as in claim 1 wherein the resulting minicell-producing K99+*E. coli* strain is *E. coli* GK500.

3. A method as in claim 1 wherein the mixed cells are incubated at a cell density of approximately $2-3 \times 10^8$ cells/ml culture medium.

4. A method as in claim 1 wherein the mixed cells are incubated at 37° C.

5. A method as in claim 1 wherein the mixed cells are incubated for about 18 hours.

6. A method as in claim 1 wherein the second culture medium is an agar plate containing streptomycin.

7. A method as in claim 6 wherein the second culture medium is an agar plate containing 200 μg/ml streptomycin.

8. A method of making a vaccine useful for preventing neonatal diarrhea in cattle comprising the steps of:

tranferring the K99 plasmid from an enteropathogenic *E. coli* strain into a minicell-producing *E. coli* strain;

growing the resulting minicell-producing K99+*E. coli* strain in broth culture medium under aerobic conditions with agitation;

separating the bacterial cells from the broth culture medium by centrifugation and suspending them; and separating minicells from complete reproductive cells by sucrose gradient centrifugation.

9. A method as in claim 8 wherein the minicell-producing K99+*E. coli* strain is *E. coli* GK500.

10. A method as in claim 8 wherein the broth culture medium is a minimal salts based synthetic medium.

11. A method as in claim 8 wherein the minicell-producing K99+*E. coli* strain is incubated for 15 to 18 hours at 36° to 37.5° C.

12. A method as in claim 8 wherein the minicell-producing K99+*E. coli* strain is incubated for 15 to 18 hours at 37° C.

13. A method as in claim 8 wherein the centrifuged bacterial cells are suspended in a buffered salt solution.

14. A method as in claim 8 further comprising the steps of:

layering the suspension containing the bacterial cells on a first sucrose gradient and centrifuging;

collecting and concentrating the top fractions of the first sucrose gradient;

layering the concentrated fractions on a second sucrose gradient and centrifuging; and collecting and concentrating the top fractions of the second sucrose gradient.

15. A method as in claim 14 wherein the first sucrose gradient comprises a 5% sucrose solution layered over a 20% sucrose solution.

16. A method as in claim 14 wherein the second sucrose gradient comprises a linear sucrose gradient of 10-5% layered over a 10% sucrose solution.

17. A method of making a vaccine which contains metabolically active, non-reproductive, anucleated live K99+*E. coli* cells and which is useful for preventing neonatal diarrhea in cattle comprising the steps of:

mixing an E. coli strain which produces metabolically active, non-reproductive, anucleated live cells (minicells) with a K99+ enteropathogenic *E. coli* strain;

incubating the mixed cells at a cell density of approximately 2 to $3 \times 10^8$ cells/ml culture medium at 37° C. for about 18 hours;

separating minicell-producing *E. coli* cells which contain the K99 plasmid from other cells in the culture medium;

growing the separated minicell-producing K99+*E. coli* GK500 cells on agar plates containing 200 μg/ml streptomycin;

selecting colonies of minicell-producing K99+*E. coli* GK500 and growing them in a minimal salts based synthetic medium for 15 to 18 hours at 36° to 37.5° C. under aerobic conditions with agitation;

separating the bacterial cells from the synthetic medium by centrifugation and suspending them in a buffered salt solution;

layering the suspension containing the bacterial cells on a first sucrose gradient, comprising a 5% sucrose solution layered over a 20% sucrose solution, and centrifuging;

collecting and concentrating the top fractions of the first sucrose gradient;

layering and concentrated fractions on a second sucrose gradient, comprising a linear sucrose gradient of 10-5% layered over a 10% sucrose solution, and centrifuging; and collecting, combining and concentrating the top fractions of the second sucrose gradient.

18. A method as in claim 14 further comprising the steps of:

freezing the combined concentrated top fractions of the second sucrose gradient at −20° C. for at least 2 to 3 days followed by thawing at room temperature; and centrifuging the thawed suspension and resuspending the pellet.

19. A method as in claim 18 wherein the combined concentrated top fractions of the second sucrose gradient are frozen at −20° C. for 9 to 10 days.

20. A method as in claim 18 wherein the pellets are resuspended in a buffered salt solution.

21. A method as in claim 14 further comprising the steps of:

incubating the combined concentrated top fractions of the second sucrose gradient in brain heart infusion broth followed by the addition of penicillin G and further incubation;

centrifugation of the incubated suspension and resuspension of the pellet.

22. A method as in claim 21 wherein the combined concentrated top fractions of the second sucrose gradient are incubated in brain heart infusion broth at 36° to 38° C. for 1 hour followed by the addition of 0.5-1.0 mg/ml of penicillin G and further incubation at 36° to 38° C. for at least 1.5 to 2 hours.

23. A method as in claim 21 wherein the pellets are resuspended in a buffered salt solution.

* * * * *